United States Patent [19]

Urueta

[11] Patent Number: 5,643,256
[45] Date of Patent: Jul. 1, 1997

[54] GOLD-PLATED ELECTROSURGICAL INSTRUMENT

[76] Inventor: R. Wilfrido Urueta, 7010 S. Santa Clara Ave., Tucson, Ariz. 85706

[21] Appl. No.: 445,276

[22] Filed: May 19, 1995

[51] Int. Cl.⁶ .................................................. A61B 17/39
[52] U.S. Cl. .................................. 606/45; 606/41; 606/39
[58] Field of Search ........................... 606/32–34, 37–42, 606/45–52

[56] References Cited

U.S. PATENT DOCUMENTS

| | | | |
|---|---|---|---|
| 4,248,231 | 2/1981 | Herczog et al. | 606/50 |
| 4,785,807 | 11/1988 | Blanch | 606/37 |
| 5,197,962 | 3/1993 | Sansom et al. | 606/45 |
| 5,308,311 | 5/1994 | Eggers et al. | 606/28 |
| 5,352,222 | 10/1994 | Rydell | 606/37 |
| 5,380,320 | 1/1995 | Morris | 606/33 |

Primary Examiner—Angela D. Sykes
Assistant Examiner—Michael Peffley
Attorney, Agent, or Firm—Benman Collins & Sawyer

[57] ABSTRACT

An electrosurgical instrument and method for making and using the same is provided. The electrosurgical instrument includes a stainless steel blade whose surface is plated with an intermediate layer comprising a substantially non-toxic metal having a hardness of at least about 130 on a Knoop scale and an electrical resistivity not exceeding about 15 microhm-cm at 20° C., with the intermediate layer having a non-stick coating. The non-stick coating prevents tissue from sticking to the instrument during surgery while the intermediate metal layer enhances the electrical conductivity of the instrument for more efficient cauterization of tissue with less power consumption. The combination of an intermediate metal layer with an outer non-stick coating eliminates the need to choose between quick and efficient cauterization during surgery and the prevention of tissue sticking to the instrument.

23 Claims, 1 Drawing Sheet

1

GOLD-PLATED ELECTROSURGICAL INSTRUMENT

BACKGROUND OF THE INVENTION

1. Field of the Invention

The present invention relates to the plating of electrosurgical instruments, and, more particularly, to the plating of the steel blade of an electrosurgical instrument with an intermediate metal layer to enhance electrical conductivity.

2. Description of Related Art

Electrosurgical knives or blades currently utilized by surgeons essentially comprise a surgical steel cutting tool, such as a scalpel, and a source of radio-frequency electrical energy for application to the cutting tool. When used in surgery, the surgeon controls the application of radio-frequency electrical energy to the blade to generate heat and cause hemostasis as tissue is cut. In this manner, bleeding is minimized during surgery.

While proven effective for controlling bleeding during surgery, electrosurgical knives are rendered less efficient by the sticking of tissue to the blade such that replacement of the blade is ultimately necessary. A common approach in addressing this problem has been to coat the blade with some type of non-stick material to which the cauterized tissue is less likely to adhere. However, the non-stick coating must not prevent the passage of sufficient electrical current from the blade to the tissue to achieve hemostasis.

Methods currently employed to achieve reduced sticking to tissue in electrically-conductive electrosurgical blades are directed to the configuration of the non-stick coating. For example, U.S. Pat. No. 4,785,807 discloses an electrosurgical knife in which the thickness of the non-stick coating is limited to about 3 mils so that the knife remains conductive. While the electrical conductivity of a steel blade having a thin non-stick coating is undoubtedly improved over one having a thicker coating, the electrical conductivity remains impeded to a degree. Other methods involve providing small, interspersed conductive openings in a non-stick coating to expose the metallic knife blade to the tissue and ensure the passage of electrical current from the blade to the tissue. However, these openings typically become coated with charred tissue such that the knives are rendered non-conductive and unusable.

It is therefore desired to provide an electrosurgical knife having both a reduction in sticking and an optimal electrical conductivity. Further, the knife must be readily cleaned and easy to manufacture.

SUMMARY OF THE INVENTION

In accordance with the present invention, an electrosurgical instrument having enhanced electrical conductivity is provided, along with a method for making and using the same. More specifically, the present electrosurgical instrument is provided with a gold strike layer and an intermediate, low-resistive, non-toxic metal layer to achieve optimal conduction of electrical energy through the instrument to tissue during surgery. An outer non-stick coating is also provided to reduce the sticking of tissue. Thus, the present electrosurgical instrument comprises:

(a) a stainless steel portion capable of conducting electric current and having at least one flesh-contacting surface formed thereon;

(b) a gold strike layer on the flesh-contacting surface;

(c) an intermediate layer on the gold-strike layer, the intermediate layer comprising a substantially non-toxic metal having a hardness of at least about 130 on a Knoop scale and an electrical resistivity not exceeding about 15 microhm-cm at 20° C.; and (d) a non-stick coating on the intermediate layer.

Thus, the resulting electrosurgical instrument retains the non-stick features of prior art instruments while exhibiting increased electrical conductivity to more efficiently and quickly cauterize tissue. The benefits realized from this increased conductivity are significant. First, the present electrosurgical instrument achieves cleaner cuts in surgery since a lower voltage may be more specifically directed that a higher voltage. Accordingly, patients sustain less tissue damage given the cleaner cuts. Second, the reduction in required voltage means that the electrosurgical equipment poses a lesser fire hazard. Third, lower voltage translates to a reduced chance of burns from the negative ground pad. Finally, a cost savings is realized in operating the present instrument, since it consumes less power than electrosurgical instruments lacking an intermediate metal layer.

DESCRIPTION OF THE PREFERRED EMBODIMENTS

Figure 1:
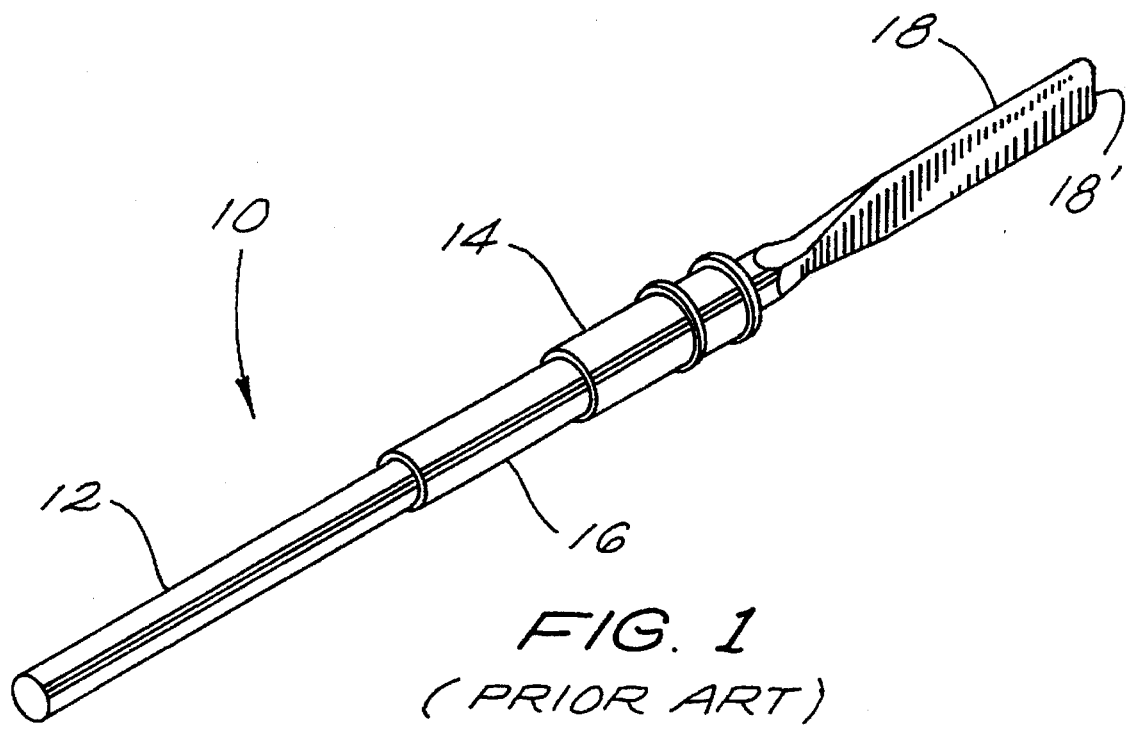
FIG. 1 is a perspective view of a conventional electrosurgical knife.

Referring to FIG. 1, there is shown a conventional electrosurgical instrument to which is applied electrical energy in the form of a radio-frequency signal for purposes of cauterizing or producing hemostasis simultaneously as tissue is cut during surgery. The knife 10 includes a proximal end 12 which is fitted into a holder to enable a surgeon to more readily hold and guide the knife. A sleeve fitting 14 is positioned around the knife shank 16, which is typically made of insulating rubber, to facilitate holding of the knife by the holder. The knife also includes a distal end 18 formed in the shape of a cutting blade 18'.

In the practice of the present invention, the distal end 18 is coated with an intermediate layer of metal having low contact resistance, sufficient hardness, and substantially no toxicity. In general, the electrical resistance of the metal should not exceed about 15 microhm-cm at 20° C., in comparison to stainless steel type 304, which has an electrical resistance of about 72 microhm-cm. The hardness of the metal should measure at least 130 on a Knoop scale to provide a sufficiently hard layer for use in surgery. Finally, the metal must meet federal guidelines for medical use in this manner, hence the requirement that the metal be substantially non-toxic. Three metals are known to meet the requirements for the intermediate layer, namely, gold, rhodium, and palladium, of which gold is preferred, having a hardness ranging from about 130 to 180 on a Knoop scale and an electrical resistivity of about 2.35 at 20° C. However, it should be understood that any metal meeting these three requirements may be employed in the practice of the invention.

A non-stick coating is then applied to the intermediate layer in the practice of the invention. By coating the stainless steel cutting blade of an electrosurgical instrument in the manner of the invention, the non-stick features of prior art designs are retained while the electrical conductivity of the instrument is enhanced for more efficient, less power-consuming cauterization during surgery.

Figure 2:
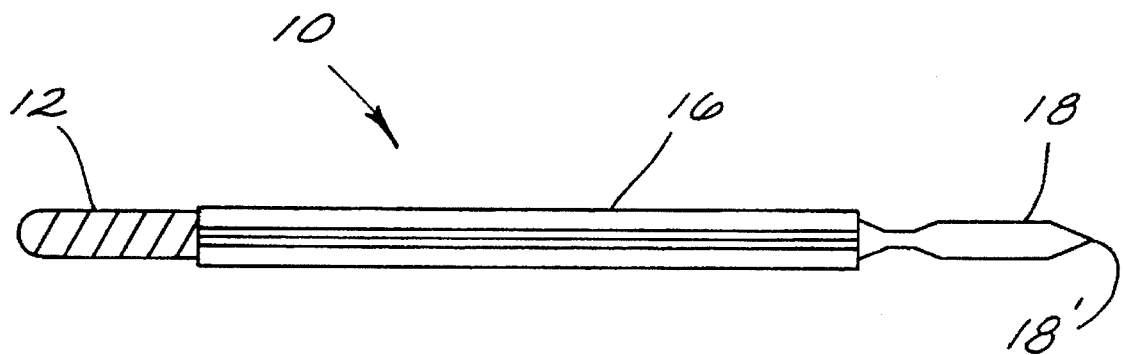
FIG. 2 is a plan view of an electrosurgical knife having a pointed blade and made in accordance with the principles of the invention.

Although a specific surgical instrument construction is shown in FIG. 1, it should be understood that a variety of electrosurgical instruments could make use of and benefit from the intermediate metal layer as will be further described hereafter. For example, the electrosurgical instrument of FIG. 2, which has a pointed cutting blade 18' as opposed to the rounded cutting blade 18' of the electrosurgical instrument in FIG. 1, is also benefited by the practice of the invention. Other examples of electrosurgical instruments benefited in the practice of the invention include those employed in such procedures as laparoscopies. In general, any instrument intended to conduct electrical energy to contacted tissue may be improved as described herein.

The plating of an intermediate metal layer such as gold, rhodium, or palladium onto the stainless steel of an electrosurgical instrument may be accomplished by any of the known techniques using commercially-available plating baths. Regardless of the choice of metal, the stainless steel surface of the distal end 18 must be prepared for plating. In general, the surface is first cleaned to remove grease, oils, oxides, and other contaminants. Then, the surface is plated with a thin layer of metal, preferably gold, in a strike process to lay the foundation for the intermediate metal layer. The intermediate metal is then plated on top of the strike layer to a thickness preferably exceeding about 100 micro-inches (0.000254 cm). Finally, a non-stick coating is deposited atop the intermediate metal layer. Each of these steps is described below in further detail.

In the specific process of the invention, the stainless steel portion of the electrosurgical instrument to be prepared for contact with tissue is first cleaned to remove grease and oils, typically by immersion in a non-etching, hot alkaline cleaner. An example of such a cleaner is the electrolytic cleaner Oakite 90 available from Oakite Chemical. Other suitably employed hot alkaline cleaners include commercially available products such as dishwashing compositions; CHEMIZID 740, an aqueous solution of sodium hydroxide and sodium lauryl sulfate available from Allied-Kelite; and ALKANOX, an acid-based cleaner having a proprietary composition available from VWR Scientific. In the practice of the invention, Oakite 90 is preferably employed as an aqueous solution ranging in concentration from about 5 to 14 oz./gal. (37 to 105 g/L), with the solution having an applied voltage ranging from about 4 to 6 volts. The Oakite 90 solution bath is preferably operated at a temperature ranging from about 140° to 160° F. (60° to 71° C.) and a pH ranging from about 13.2 to 13.4. Immersion time typically ranges from about 1 to 2 minutes. If the part is very oily or greasy, a solvent degrease step may be inserted prior to the alkaline cleaning step. Following the alkaline cleaning step, the cleaned parts are rinsed in cold running water.

The alkaline-cleaned portion of the instrument is then cleaned with an acid to remove remaining oxides and contaminants not removed by the alkaline cleaning step. Any of the acid etches known for removing oxides may be employed, such as a 50 vol % solution of saturated hydrochloric acid in water. Another suitably employed acid-etch solution comprises ammonium bifluoride double salt, commercially-available from Allied Kelite under the tradename ARP 28. The hydrochloric acid solution is preferably employed in the practice of the invention, with an immersion time of about 20 to 30 seconds typically being sufficient. Following the acid-etch step, the cleaned parts are again rinsed in cold running water.

The cleaned electrosurgical blade is now ready for plating with a thin strike layer which provides a surface to which the intermediate layer may subsequently adhere. The strike layer also serves to prevent oxides from reforming after the acid etch step. Preferably, the strike layer comprises gold, which may be achieved by at least two alternate methods in the practice of the invention: (1) performing an acid gold strike, or (2) performing a nickel strike followed by a gold strike.

In the event an acid gold strike is performed to achieve the gold strike layer, the cleaned electrosurgical blade is immersed in an acid gold strike bath and gold is electroplated onto the blade. The resulting gold layer preferably ranges in thickness from about 0.000003 to 0.00005 inch (0.0000076 to 0.00013 cm). A thickness of less than about 0.000003 inch may not achieve sufficient adherence of the subsequently-plated intermediate metal layer thereto, and a thickness of more than about 0.00005 inch may be too brittle.

Any of the known acid gold strike baths may be employed in the practice of the invention, and the bath is typically operated at about room temperature. Preferably, an acid gold strike bath available from Technic, Inc. (Anaheim, Calif.) is employed, the acid gold bath having a proprietary composition comprising gold and hydrochloric acid. In the operation of Technic's acid gold strike bath, gold metal is added to the bath solution as needed to maintain a gold concentration of about 0.25 tr.oz./gal. (2.05 g/L). The Technic acid gold strike bath solution is preferably operated at a temperature ranging from about 80° to 120° F. (27° to 49° C.) and at a pH of less than about 1.0, as controlled by the presence of hydrochloric acid. In the event a rack method is employed as opposed to a barrel method, a current of about 50 to 150 amps/ft$^2$ (538 to 1,614 amps/m$^2$) is impressed on the part, which serves as the cathode. The optimal current density depends upon the particular parameters of the plating tank employed, such as its size and material. A typical dwell time of about 1 to 3 minutes is required to reach the desired range of thickness, with the optimum dwell time depending upon the desired thickness of gold as well as the level of current employed. The optimization of current density and dwell time is considered to be a routine endeavor that is well within the capabilities of those having ordinary skill in the art and is not considered to be undue.

In the event a nickel strike and subsequent gold (non-"acid") strike are performed to achieve the thin gold strike layer atop the stainless steel of the instrument, both the resulting nickel layer and thin gold layer preferably range in thickness from about 0.000003 to 0.00005 inch (0.0000076 to 0.00013 cm). A thickness of less than about 0.000003 inch may not achieve sufficient adherence of the subsequently-plated intermediate metal layer thereto, and a thickness of more than about 0.00005 inch may be too brittle.

In the practice of the invention, the nickel strike process entails immersing the cleaned electrosurgical blade into a nickel plating bath then electroplating nickel onto the blade in the presence of a nickel anode. Any of the known chloride nickel strike baths may be employed in the practice of the invention, and the bath is typically operated at about room temperature. Preferably, the nickel plating bath comprises an aqueous solution of nickel chloride and hydrochloric acid, with the nickel chloride ranging in concentration from about 26 to 48 oz./gal. (210 to 359 g/L) and the hydrochloric acid ranging in concentration from about 20 to 70 oz./gal. (150 to 524 g/L). Preferably, nickel chips serve as the anode. A current of about 15 to 30 amps/ft$^2$ (161 to 323 amps/m$^2$) is impressed on the part, which serves as the cathode. The optimal current density depends upon the particular parameters of the plating tank employed, such as its size and material. A typical dwell time of about 2 to 3 minutes is required to reach the desired range of thickness, with the optimum dwell time depending upon the desired thickness of nickel as well as the level of current employed. The optimization of current density and dwell time is considered to be a routine endeavor that is well within the capabilities of those having ordinary skill in the art and is not considered to be undue.

If a nickel strike layer has been deposited, a gold strike process (as opposed to an acid gold strike process) is then performed to deposit a thin gold strike layer as a precursor to the subsequent electroplating of an intermediate metal layer. In the practice of the invention, the gold strike process entails immersing the cleaned electrosurgical blade into a gold plating bath and then electroplating gold onto the blade. Any of the known gold strike baths capable of depositing gold atop nickel may be employed in the practice of the invention. Preferably, the gold plating bath is an aqueous solution comprising gold metal, potassium cyanide, and dipotassium phosphate, with the gold metal ranging in concentration from 0.056 to 0.20 tr.oz./gal (0.46 to 1.64 g/L), potassium cyanide ranging in concentration from about 0.18 to 0.31 oz./gal. (1.35 to 2.32 g/L), and dipotassium phosphate ranging in concentration from about 1.75 to 2.5 oz./gal. (13.1 to 18.7 g/L). Also preferably, gold metal is simply added to the solution as necessary throughout the plating process, as opposed to employing a gold metal anode. A current of about 2 to 4 amps/ft$^2$ (21.5 to 43.1 amps/m$^2$) is impressed on the part, which serves as the cathode. The gold strike bath is preferably operated at a temperature ranging from about 140° to 150° F. (60° to 66° C.) and a pH ranging from about 9.5 to 12.0. Typically, a dwell time of about 5 to 10 seconds is required to reach the desired range of thickness, with the optimum dwell time depending upon the desired thickness of gold as well as the level of current employed. The optimization of current density and dwell time is considered to be a routine endeavor that is well within the capabilities of those having ordinary skill in the art and is not considered to constitute undue experimentation.

Addition agents such as wetters and brighteners may be included in the acid strike, nickel strike, or gold strike baths to enhance the strike characteristics. The composition and concentration of such addition agents are well-known in the art and hence do not form a part of this invention. At the conclusion of the deposition of a thin strike layer, the part is rinsed in cold running water in preparation for electroplating an intermediate metal layer.

Once a thin strike layer is in place, the intermediate metal layer may then be electroplated to a preferred thickness of at least about 100 micro-inches (0.000254 cm). A thickness of less than about 100 micro-inches would likely not be sufficiently hard. Regardless of whether gold, rhodium, or palladium is chosen to serve as the intermediate layer, there are known techniques and electroplating baths to electroplate such a layer. Any of such known techniques may be employed in the practice of the invention to provide an intermediate metal layer atop the thin strike layer. Since the intermediate metal layer preferably comprises gold, further detail is provided below regarding the process of electroplating gold onto the strike layer. It is expected that the process for electroplating rhodium or palladium onto the strike layer would be analogous.

To electroplate an intermediate layer of gold atop the strike layer, the portion of the instrument to be plated is immersed in a gold electroplating bath, preferably according to a rack method. Any of the known gold electroplating baths may be employed in the practice of the invention.

Preferably, Techni Gold—25, a proprietary non-cyanide gold plating bath commercially-available from Technic, Inc., is employed in the practice of the invention to achieve a gold layer having a hardness ranging from about 130 to 180 on a Knoop scale. Rather than employ a gold metal anode, gold metal is preferably added to the solution as necessary throughout the plating process. A current of about 3 to 5 amps/ft$^2$ (32.3 to 53.8 amps/m$^2$) is impressed on the part, which serves as the cathode. Typically, a dwell time of about 12 minutes is required to plate about 100 micro-inch of gold using the Techni-Gold 25 bath in a rack method. The optimization of current density and dwell time is considered to be a routine endeavor that is well within the capabilities of those having ordinary skill in the art and is not considered to be undue. The Techni Gold—25 gold plating bath is preferably operated at a temperature ranging from about 120° to 140° F. (49° to 60° C.) and a pH ranging from about 8.8 to 10.7, with the pH being preferably adjusted using a 20% solution of sodium hydroxide.

Addition agents such as wetters and brighteners may also be included in the gold electroplating bath to enhance the plating characteristics. For example, a brightener permits use of higher current densities to achieve a harder deposit. The composition and concentration of such addition agents are well-known in the art and hence do not form a part of this invention.

Following the electroplating of the intermediate metal layer, a hot water rinse may be used if needed to remove contaminants. Finally, the electrosurgical instrument may be dried, preferably with compressed air, in preparation for the application of a non-stick surface.

That portion of the electrosurgical instrument that has been plated with an intermediate metal layer is then coated with a non-stick material comprising a fluoropolymer material, with the fluoropolymer material preferably preceded by a coating of liquefied primer material. Any of the primer materials commonly used as precursors to fluoropolymer material for electrosurgical instruments may be employed in the practice of the invention, such as primer materials commercially available from Whitford Corp. and DuPont. For aesthetic purposes, it is preferable that the primer coating be clear such that the underlying metal is visible. Preferably, the primer material is sprayed onto the metal-plated portion of the instrument using, for example, an airbrush technique.

After the primer material is dried, the blade is placed in a kiln oven for less than about 5 minutes (preferably about 1 minute) at a temperature ranging from about 450° to 850° F. (232° to 455° C.). The optimum temperature within this range depends upon the particular primer material employed. After removal from the oven, the blade and primer material are allowed to cool to room temperature.

Finally, a coat of fluoropolymer material is applied to the primer material. Suitably employed fluoropolymer materials include, but are not limited to polytetrafluoroethylene (PTFE) and fluorinated ethylenepropylene resin (FEP). Preferably, the fluoropolymer material is sprayed onto the primer material, or in the absence of primer material, directly onto the intermediate metal layer. An air brush may be employed to effect a spray. After applying the fluoropolymer material, the blade and material are preferably allowed to dry for about one hour at room temperature. The blade is then placed in a preheated oven for less than about 5 minutes (preferably about 1 minute) at a temperature ranging from about 450° to 850° F. (232° to 455° C.). The optimum temperature within this range depends upon the particular fluoropolymer material employed. After removal from the oven, the coated blade is allowed to cool to room temperature. Upon cooling, the blade may be polished to a high sheen using a soft cotton cloth to remove dirt and debris.

The total thickness of the non-stick coating is preferably about 0.002 inch (0.005 cm). The non-stick coating as defined herein includes both the primer material and the fluoropolymer material. Thus, if a coat of fluoropolymer material is employed alone, it preferably has a thickness of about 0.002 inch. Alternatively, if both a primer coat and fluoropolymer coat are employed as the non-stick coating, the non-stick coating preferably has a total thickness of about 0.002 inch. If the non-stick coating is too thick, it may be too soft and might be susceptible to cracking. On the other hand, if the non-stick coating is too thin, incomplete coverage of the intermediate gold layer may result.

The electrosurgical instrument manufactured and used in accordance with the present invention eliminates the need to choose between quick and efficient cauterization during surgery and the prevention of tissue sticking to the instrument. Rather, the present instrument retains the non-sticking capabilities of the prior art while enhancing the electrical conductivity of the instrument with gold plating. As such, the length of time required for cauterization is minimized as is the amount of power necessary to achieve cauterization. Furthermore, the process by which the present electrosurgical instrument is manufactured is relatively simple and easily automated.

EXAMPLES

A comparison has been made between three electrosurgical instruments to illustrate the advantages realized in the practice of the invention. The stainless steel blades of the three electrosurgical instruments were prepared for testing as follows:

- Electrosurgical instrument "A": The stainless steel blade remained uncoated.
- Electrosurgical instrument "B": The stainless steel blade was coated with Teflon™ in accordance with the teachings of U.S. Pat. No. 4,785,807.
- Electrosurgical instrument "C": The stainless steel blade was sequentially coated with a thin acid gold strike layer, a layer of gold having a thickness of about 100 micro-inch, a primer coat, and a polytetrafluoroethylene coating, all in accordance with the present invention.

The three instruments were each employed in surgical procedures. The quantity of electrical energy made available to the instruments for purposes of inducing hemostasis during surgery was controlled by a power dial having an uncalibrated range from 1 to 10. Thus, while the particular amount of watts employed for each instrument is unknown, the power dial setting indicates in relative terms the amount of electrical energy required such that a comparison between instruments may be made. Observations regarding power settings, tissue sticking, and tissue damage follow for each instrument.

Electrosurgical instrument "A": This instrument required power settings ranging from about 3 to 7 to achieve hemostasis during surgery. Without a non-stick coating of any sort, this instrument sustained extensive tissue sticking such that the surgeon had to frequently clean the instrument during surgery, thus increasing the time of surgery.

Electrosurgical instrument "B": This instrument required power settings ranging from about 5 to 10 to achieve hemostasis, which is considerably more wattage than that required for instrument "A". As a result of the increased wattage, more tissue damage was sustained compared with instrument "A". Further, the increased voltage elevated the fire hazard associated with employing an electro surgical instrument. On the other hand, less tissue adhered to the Teflon™-coated blade than the bare stainless steel blade of instrument "A", and any tissue that perchance did adhere to blade "B" was readily cleaned. Thus, less surgical time was expended cleaning instrument "B" than instrument "A".

Electrosurgical instrument "C": This instrument required power settings ranging from about 3 to 6, which was a considerable improvement over the Teflon™-coated instrument "B" and even a slight improvement over the bare stainless steel blade of instrument "A". The gold interlayer provided a more concentrated power source for hemostasis so that cuts were cleaner. Accordingly, the amount of tissue damage observed for instrument "C" was comparable to that of instrument "A" and much less than that of instrument "B". Further, like instrument "B", this instrument experienced little tissue adherence given its non-stick coating, and any tissue that did stick was readily cleaned.

In sum, it has been illustrated that an electrosurgical instrument made in accordance with the present invention combines the advantages of prior art instruments while eliminating their significant disadvantages. More specifically, electrosurgical instrument "C" conducted electrical energy at least as well as the bare stainless steel blade of electrosurgical instrument "A" so that lower power was possible to achieve hemostasis during surgery, thereby inflicting less tissue damage and posing a lesser fire hazard. Further, electrosurgical instrument "C" also exhibited a lesser tissue adherence on par with the Teflon™-coated blade of instrument "B".

Essentially, it has been demonstrated that an electrosurgical instrument made in accordance with the present invention enables a surgeon to take advantage of a non-stick coating without subjecting patients to increased tissue damage deriving from the use of a diffused power source to achieve hemostasis.

Thus, there has been disclosed an electrosurgical instrument having an intermediate metal layer topped by a non-stick coating. A method of enhancing the electrical conductivity of an electrosurgical instrument is also disclosed, along with a method of using the resulting electrosurgical instrument. It will be appreciated by those skilled in the art that various changes and modifications of an obvious nature may be made, and all such changes and modifications are considered to fall within the scope of the invention, as defined by the appended claims.

What is claimed is:

1. An electrosurgical instrument to which electric current can be applied for cauterizing tissue, said electrosurgical instrument comprising:
   (a) a stainless steel portion capable of conducting said electric current and having at least one flesh-contacting surface formed thereon;
   (b) a gold strike layer on said at least one flesh-contacting surface;
   (c) an intermediate layer on said gold-strike layer, said intermediate layer comprising a substantially non-toxic metal having a hardness of at least about 130 on a Knoop scale and an electrical resistivity not exceeding about 15 microhm-cm at 20° C.; and
   (d) a non-stick coating on said intermediate layer.

2. The electrosurgical instrument of claim 1 wherein said gold strike layer ranges from about 0.000003 to 0.00005 inch in thickness.

3. The electrosurgical instrument of claim 1 wherein said intermediate layer has a thickness of at least 0.0001 inch and comprises a metal selected from the group consisting of gold, rhodium, and palladium.

4. The electrosurgical instrument of claim 3 wherein said intermediate layer comprises gold.

5. The electrosurgical instrument of claim 1 wherein said non-stick coating has a thickness of about 0.002 inch and comprises a layer of fluoropolymer material.

6. The electrosurgical instrument of claim 5 wherein said fluoropolymer material comprises polytetrafluoroethylene.

7. The electrosurgical instrument of claim 5 wherein said non-stick coating further comprises a primer coat.

8. The electrosurgical instrument of claim 7 wherein said primer coat is substantially transparent to visible light.

9. A method for enhancing the electrical conductivity of an electrosurgical instrument used with a source of electrical energy during surgery to cauterize tissue, said electrosurgical instrument comprising a stainless steel portion for receiving said electrical energy and having at least one flesh-contacting surface thereon, said method comprising:

(a) plating on said at least one flesh-contacting surface a gold strike layer;

(b) plating on said gold strike layer an intermediate layer comprising a substantially non-toxic metal having a hardness of at least about 130 on a Knoop scale and an electrical resistivity not exceeding about 15 microhm-cm at 20° C.; and (c) coating said intermediate layer with a non-stick coating, wherein said electrical energy is conducted from said at least one flesh-contacting surface to said tissue.

10. The method of claim 9 wherein said gold strike layer is formed on said at least one flesh-contacting surface by either (a) performing an acid gold strike or (b) performing a nickel strike on said at least one flesh-contacting surface and a non-acid gold strike thereover.

11. The method of claim 9 wherein said gold strike layer ranges from about 0.000003 to 0.00005 inch in thickness.

12. The method of claim 9 wherein said intermediate layer has a thickness of at least 0.0001 inch and comprises a metal selected from the group consisting of gold, rhodium, and palladium.

13. The method of claim 12 wherein said intermediate layer comprises gold.

14. The method of claim 9 wherein said non-stick coating has a thickness of about 0.002 inch and comprises a layer of fluoropolymer material.

15. The method of 14 wherein said fluoropolymer material comprises polytetrafluoroethylene.

16. The method of claim 14 wherein said non-stick coating further comprises a primer coat.

17. The method of claim 16 wherein said primer coat is substantially transparent to visible light.

18. A method of using an electrosurgical instrument having a stainless steel portion for receiving electrical energy and having at least one flesh-contacting surface thereon, said at least one flesh-contacting surface having been plated with a gold strike layer upon which an intermediate layer has been plated comprising a substantially non-toxic metal having a hardness of at least about 130 on a Knoop scale and an electrical resistivity not exceeding about 15 microhm-cm at 20° C., said intermediate layer having been coated with a non-stick coating, said method comprising:

(a) providing said electrosurgical instrument for use during surgery;

(b) cutting tissue during surgery with said at least one flesh-contacting surface of said electrosurgical instrument having said intermediate layer and said non-stick coating thereon; and (c) cauterizing said cut tissue by providing said at least one flesh-contacting surface with electrical energy to conduct to said cut tissue through said intermediate layer and said non-stick coating, wherein said intermediate layer enhances the ability of said at least one flesh-contacting surface to conduct electrical energy to said cut tissue through said non-stick coating.

19. The method of claim 18 wherein said intermediate layer has a thickness of at least 0.0001 inch and comprises a metal selected from the group consisting of gold, rhodium, and palladium.

20. The method of claim 19 wherein said intermediate layer comprises gold.

21. The method of claim 18 wherein said non-stick coating has a thickness of about 0.002 inch and comprises a layer of fluoropolymer material.

22. The method of 21 wherein said fluoropolymer material comprises polytetrafluoroethylene.

23. The method of claim 21 wherein said non-stick coating further comprises a primer coat.

* * * * *